(12) United States Patent
Yokokawa et al.

(10) Patent No.: US 10,168,345 B2
(45) Date of Patent: Jan. 1, 2019

(54) AUTOMATIC ANALYSIS APPARATUS AND SAMPLE MEASURING METHOD

(71) Applicant: Hitachi High-Technologies Corporation, Minato-ku, Tokyo (JP)

(72) Inventors: Akiko Yokokawa, Tokyo (JP); Tomonori Mimura, Tokyo (JP); Sakuichiro Adachi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 409 days.

(21) Appl. No.: 14/411,304

(22) PCT Filed: May 30, 2013

(86) PCT No.: PCT/JP2013/065038
§ 371 (c)(1),
(2) Date: Dec. 24, 2014

(87) PCT Pub. No.: WO2014/002677
PCT Pub. Date: Jan. 3, 2014

(65) Prior Publication Data
US 2015/0160251 A1    Jun. 11, 2015

(30) Foreign Application Priority Data
Jun. 25, 2012    (JP) .................. 2012-142135

(51) Int. Cl.
*G01N 35/10*    (2006.01)
*G01N 21/25*    (2006.01)
(Continued)

(52) U.S. Cl.
CPC ....... *G01N 35/1002* (2013.01); *G01N 21/253* (2013.01); *G01N 21/274* (2013.01);
(Continued)

(58) Field of Classification Search
None
See application file for complete search history.

(56) References Cited

U.S. PATENT DOCUMENTS 6,707,043 B2   3/2004   Coates et al.
6,791,676 B1   9/2004   Meller
(Continued)

FOREIGN PATENT DOCUMENTS

EP   2 444 794 A1   4/2012
JP   5-180761 A     7/1993
(Continued)

OTHER PUBLICATIONS

International Preliminary Report on Patentability (PCT/IB/338 & PCT/IB/373) dated Jan. 8, 2015, including Written Opinion (PCT/ISA/237) (Eight (8) pages).
(Continued)

*Primary Examiner* — Benjamin R Whatley
(74) *Attorney, Agent, or Firm* — Crowell & Moring LLP

(57) ABSTRACT

An automatic analysis apparatus capable of improving detection sensitivity is provided. An optimum photometer between a light-scattering photometer and an absorptiometer based on a concentration range may be decided. A standard solution is measured multiple times at a normal calibration and a calibration curve is created. Calibration curves are individually created for an absorptiometer and a light-scattering photometer from the minimum and maximum measured values of the concentrations of each standard solution. The upper and lower limits of a standard solution concentration are computed from the minimum/maximum calibration curves. Sensitivity may be computed by using calibration parameters. Whether to use a concentration by absorption or a concentration by scattered light is decided based on the computed sensitivity. The computed sensitivities are compared between the concentration by absorption (Continued)

and the concentration by scattered light, and the use of the concentration of a higher sensitivity is decided.

3 Claims, 13 Drawing Sheets

(51) Int. Cl.
  *G01N 21/51* (2006.01)
  *G01N 21/82* (2006.01)
  *G01N 21/27* (2006.01)
  *G01N 35/00* (2006.01)
  *G01N 35/02* (2006.01)

(52) U.S. Cl.
  CPC ............ *G01N 21/51* (2013.01); *G01N 21/82* (2013.01); *G01N 35/00623* (2013.01); *G01N 35/00693* (2013.01); *G01N 35/025* (2013.01); *Y10T 436/115831* (2015.01)

(56) References Cited

U.S. PATENT DOCUMENTS

| | | | |
|---|---|---|---|
| 6,846,457 B1 * | 1/2005 | Tokiwa | ............ G01N 35/00594 422/63 |
| 2005/0168737 A1 | 8/2005 | Bradshaw et al. | |
| 2007/0231208 A1 * | 10/2007 | Tanaka | ............. G01N 35/00603 422/67 |
| 2008/0070318 A1 * | 3/2008 | Yamamoto | ............. G01N 21/31 436/164 |
| 2011/0032516 A1 | 2/2011 | Zhou et al. | |
| 2012/0000268 A1 | 1/2012 | Li et al. | |
| 2012/0282139 A1 * | 11/2012 | Makino | .................. G01N 21/51 422/73 |
| 2013/0108509 A1 * | 5/2013 | Shiba | ..................... G01N 21/51 422/82.05 |
| 2013/0266484 A1 * | 10/2013 | Kamihara | ........ G01N 35/00613 422/82.09 |

FOREIGN PATENT DOCUMENTS

| | | | |
|---|---|---|---|
| JP | 5-196503 A | | 8/1993 |
| JP | 6-308074 A | | 11/1994 |
| JP | 10-160668 A | | 6/1998 |
| JP | 10-332582 A | | 12/1998 |
| JP | 10332582 A | * | 12/1998 |
| JP | 11-344439 A | | 12/1999 |
| JP | 2001-141654 A | | 5/2001 |
| JP | 2001-238859 A | | 9/2001 |
| JP | 2005-233627 A | | 9/2005 |
| JP | 3128163 U | | 12/2006 |
| JP | 2007-522446 A | | 8/2007 |
| JP | 2008-8794 A | | 1/2008 |
| JP | WO 2012066891 A1 * | 5/2012 | ....... G01N 35/00613 |
| WO | WO 2011/162113 A1 | | 12/2011 |

OTHER PUBLICATIONS

International Search Report (PCT/ISA/210) dated Aug. 6, 2013 with English-language translation (Four (4) pages).
Extended European Search Report issued in counterpart European Application No. 13809593.0 dated Jan. 29, 2016 (eight (8) pages).

* cited by examiner

FIG. 15

APPLICATION SETTING

● ANALYSIS ○ CALIBRATION ○ STANDARD SOLUTION

ITEM NAME [IRI ▷]

SAMPLE QUANTITY [17.5]
DISPENSING REAGENT R1 [140]
QUANTITY R3 [70]

DUMMY REAGENT QUANTITY [1 ▷]
CELL DETERGENT [1 ▷]

ABSORPTIOMETER
ANALYSIS METHOD [2 POINT END ▷]
PHOTOMETRIC POINT [19] [34] [0]
WAVELENGTH: DOMINANT/ COMPLEMENTARY [800 ▷] [570 ▷]

LIGHT-SCATTERING PHOTOMETER
ANALYSIS METHOD [2 POINT END ▷]
PHOTOMETRIC POINT [20] [34] [0]
LIGHT RECEIVING ANGLE [20° ▷]

APPLICATION SETTING

○ ANALYSIS  ● CALIBRATION  ○ STANDARD SOLUTION

ITEM NAME [ IRI ▽ ]

CONCENTRATION COMPUTATION METHOD
● AUTOMATION  ○ REGION DESIGNATION  ○ SENSITIVITY PRIORITY

ABSORPTIOMETER
CALIBRATION METHOD [ SPLINE ▽ ]
POINT [ 6 ]

| | |
|---|---|
| CONVERGENCE ALLOWABLE ABSORPTION INTENSITY | 999 |
| VARIATION ALLOWABLE ABSORPTION INTENSITY | 999 |
| SENSITIVITY ALLOWABLE ABSORPTION INTENSITY | 9999 999 |
| FIRST STANDARD SOLUTION ABSORPTION INTENSITY RANGE | 9999 999 |

LIGHT-SCATTERING PHOTOMETER
CALIBRATION METHOD [ SPLINE ▽ ]
POINT [ 4 ]

| | |
|---|---|
| CONVERGENCE ALLOWABLE SCATTERED LIGHT INTENSITY | 999 |
| VARIATION ALLOWABLE SCATTERED LIGHT INTENSITY | 999 |
| SENSITIVITY ALLOWABLE SCATTERED LIGHT INTENSITY | 9999 999 |
| FIRST STANDARD SOLUTION SCATTERED LIGHT INTENSITY RANGE | 9999 999 |

25b

AUTOMATIC ANALYSIS APPARATUS AND SAMPLE MEASURING METHOD

TECHNICAL FIELD

The present invention relates to an automatic analysis apparatus for clinical examination and a sample measuring method.

BACKGROUND ART

An absorptiometer to measure a transmitted light quantity is used for an automatic analysis apparatus for clinical examination. There are two kinds of measurement principles, namely a measurement principle using the following enzyme and a measurement principle using antigen-antibody reaction, in the reaction principle of a sample and a reagent in an examination item and two kinds of major reactions, namely color reaction between a substrate and an enzyme and agglutination reaction between an antigen and an antibody, are used for the reaction of a reaction liquid.

The former is biochemical analysis and LDH (lactate dehydrogenase), ALP (alkaline phosphatase), and AST (aspartate oxoglutarate aminotransferase) are named as the examination items.

The latter is immune assay and CRP (C-reactive protein), IgG (immunoglobulin), and RF (rheumatoid factor) are named as the examination items.

The concentration of a substance in blood measured at the immune assay is low and thus a high sensitivity is required. A high sensitivity has heretofore been tried in a latex immunoagglutination method for quantitating the quantity of an ingredient contained in a sample by: using a reagent produced by sensitizing (binding) an antibody on the surface of a latex particle; projecting light to a reaction liquid when the ingredient contained in the sample is recognized and agglutinated; and measuring the quantity of the light that is not scattered by a latex aggregate and has been transmitted.

As a sample analysis apparatus to analyze the quantity of an ingredient contained in a sample, an automatic analysis apparatus to irradiate a sample or a reaction liquid produced by mixing a sample and a reagent with light from a light source, measure the quantity of the transmitted light of a single wavelength or plural wavelengths obtained resultantly and compute an absorbance, and determine an ingredient quantity from the relationship between the absorbance and a concentration in accordance with the Lambert-Beer law is widely used. In such an apparatus, a plurality of cells retaining a reaction liquid are arranged circumferentially on a cell disk repeating rotation and stop and the chronological change of an absorbance is measured at regular time intervals for about 10 minutes with a prearranged transmitted light measuring unit during the rotation of the cell disk.

In an automatic analysis apparatus for clinical examination, a method of measuring the absorbance of a reaction liquid in a reaction container while it is rotated is the mainstream. The method is called a turntable discrete method. In the method, measurement is carried out once while a reaction disk on which a reaction container is set makes one revolution. The absorbance of the reaction container is measured at regular cyclic intervals.

In the turntable discrete method, reagent dispensing is carried out multiple times (R1, R2, . . . ) in one cycle. As one cycle, there are several methods including a control method of rotating a reaction disk at one revolution and a degree corresponding to the reaction container and a control method of rotating a reaction disk at a fraction of one revolution plus a degree corresponding to the number of the reaction containers. The difference between the methods depends on the layout of a reagent dispensing mechanism and the alignment of R1, R2 stirring mechanisms.

A feature of the method is to measure a reaction liquid in a reaction container at regular intervals. Another feature thereof is to be able to monitor the reaction process between a sample and a reagent during measurement.

In an automatic analysis apparatus for clinical examination, to increase sensitivity not by measuring a transmitted light quantity with a photometer but by measuring a scattered light quantity is also attempted. When a reagent making use of antigen-antibody reaction is used, an antigen contained in a sample is reacted with an antibody contained in the reagent. A reactant is produced by antigen-antibody reaction, the particle is irradiated with light, and the magnitude of the scattered light or transmitted light is measured. A light-scattering photometer, a so-called nephelometer, is used.

For example, a system of separating transmitted light from scattered light with a diaphragm and measuring an absorbance and the scattered light simultaneously (Patent Document 1), a configuration of increasing accuracy on the higher concentration side by measuring the light reflected and scattered at a large aggregate formed as a result of the advancement of agglutination reaction (Patent Document 2), and a method of measuring the respective average light quantities of forward-scattered light and backscattered light with an integrating sphere in front of and at the back of a reaction container and correcting the turbidity change caused by the misregistration of a cell (Patent Document 3) are disclosed.

PRIOR ART DOCUMENTS

Patent Document

Patent Document 1: JP2011-141654A
Patent Document 2: JP2008-008794A
Patent Document 3: JPH10-332582A

SUMMARY OF THE INVENTION

Problem to be Solved by the Invention

As stated above, a method of mounting a light-scattering photometer and an absorptiometer on an apparatus and combining the light-scattering photometer and the like with the absorptiometer is described in Patent Documents 1 and 2.

Since sensitivity cannot be compared simply between a light-scattering photometer and an absorptiometer mounted on an apparatus however, a method of judging a concentration range and an optical system to be used that make highly accurate measurement possible has been unknown. Consequently, an automatic analysis apparatus having both a light-scattering photometer and an absorptiometer has been useless as an actual apparatus.

In a reagent based on the measurement principle of immune nephelometry or latex nephelometry, the type and characteristics of an antibody contained in the reagent, the normal value range of a measurement item, a lowest detection sensitivity, turbidity by the influence of bilirubin contained in a sample, hemolysis, and high fat, and others determine the performance of a measuring object.

In an instrument, an absorptiometer using a conventional automatic analysis apparatus and a light-scattering photometer for improving reagent sensitivity are used. Problems on the influential factors, an absorptiometer, and a light-scattering photometer are described below.

(1) Relationship Between Absorptiometer and Reagent

In an absorptiometer, a halogen lamp is used as the light source and measurement is carried out simultaneously in a plurality of wavelength regions ranging from ultraviolet to near-infrared. Measurement can be carried out while a wavelength region susceptible to the influence of hemolysis, bilirubin, and the like is avoided. The wavelength can be selected in conformity with the particle size of latex and a measurement range and linearity is also kept wide. Since light of a wide range is projected however, the measurement sensitivity at a low concentration is inferior. In the vicinity of O in particular, it is impossible to know the difference because of transmitted light.

(2) Relationship Between Light-Scattering Photometer and Reagent

Since light of a single wavelength is projected and scattered light is measured, sensitivity at a low concentration is good. In a sample of a high concentration, the diameter of an antigen-antibody product increases, multiple scattering is caused, and the measurable range is narrow. Since light of a single wavelength is projected, the diameter of a latex particle that can be appropriately measured is limited. In order to appropriately measure latex particles ranging from small diameters to large diameters however, it is necessary to prepare a plurality of light-scattering photometers having different irradiation wavelengths.

As stated above, there are several discrepancies in the combination of a method using antigen-antibody reaction, a reagent and an instrument, and an absorptiometer and a light-scattering photometer.

With regard to the measurement of an immune item, particularly of a latex reagent, the case of consolidating plural analyzers including a light-scattering photometer and the like in addition to a heretofore existing absorptiometer into an automatic analysis apparatus is examined as follows.

Since plural photometers are used in combination, data processing and the setting of analysis parameters for at least two kinds of optical systems (at least two kinds of independent analysis parameters) are required.

In an analysis apparatus having a single optical system of prior art, with regard to each of analysis items: parameters such as a sample quantity, a reagent quantity, a wavelength, a reaction time, and others are decided in accordance with an analysis method for reaction; the dispensing of a reagent and the analysis of measurement are carried out in accordance with the decided basic parameters; and a concentration is computed.

The calibration of a reagent is required prior to general patient sample analysis. In general, whether a reagent is good or bad is judged from the reaction result by using the sensitivity of the reagent and the standard solution and the variation of the sensitivity and an absorbance of the reagent. In a conventional automatic analysis apparatus, S1ABS, SENS, DUP, and so on are checked.

In another photometer such as a light-scattering photometer too, the calibration of a reagent is carried out and whether the reagent is good or not is judged. The judgment values are carried out as judgment against the measurement conditions of a relevant analysis parameter. As a method for judgment, there is a method of deciding an allowable value of each reagent lot at a reagent maker. Further as another judgment method, there is the case of judging occasionally from a calibration result.

A light-scattering photometer and an absorptiometer have fundamental features respectively. The performance comparison table of a light-scattering photometer and an absorptiometer is shown in Table 1.

TABLE 1

Performance comparison between light-scattering photometer and absorptiometer

| | Absorptiometric method | Scattered light | Transmitted light |
|---|---|---|---|
| High resolution | ○ | ⊙ | ○ |
| Linearity | ⊙ | Δ | ⊙ |
| Influence of coexisting material | | | |
| Hemolysis | ⊙ | ○ | |
| Bilirubin | ⊙ | ○ | |
| RF | ○ | ○ | |
| Turbidity | ○ | ⊙ | |

As shown in Table 1, the performance including resolution, linearity, the influence of a coexisting material, and so on is not entirely satisfied with only one type photometer.

In this way, since the full performance is not satisfied with only one type photometer, analysis is carried out by the combination of: an apparatus dedicated to immune nephelometry, which is operated with plural apparatuses having different analytical principles (light-scattering photometer); and an automatic analysis apparatus for biochemistry on which a conventional absorptiometer is mounted.

Even when an apparatus of a high sensitivity is prepared therefore, it is necessary to: change the dilution of a sample and the quantity of the sample so that a low concentration and a high concentration may be obtained for each measurement item and for each patient sample as reexamination after once the patient sample is measured; and switch between measurement with a light-scattering photometer and measurement with an absorptiometer. Consequently, workflow becomes complex and the possibility of operator's mistake increases. Further, a long examination time is required.

With one type of optical systems, the sensitivities can be compared by the outputs of the optical systems. With optical systems of different principles however, the sensitivities of the optical systems of different principles cannot be simply compared with each other. In prior art therefore, in the case of mounting two types of photometers of a light-scattering photometer and an absorptiometer on an automatic analysis apparatus, the detection sensitivity has been hardly improved because the respective detection sensitivities have been hardly compared and an optimum photometer has been decided in accordance with a concentration range.

An object of the present invention is to materialize an automatic analysis apparatus and a sample measuring method, which are capable of: deciding an optimum photometer from the two photometers of a light-scattering photometer and an absorptiometer in accordance with a concentration range; and improving detection sensitivity.

Means for Solving the Problems

In order to attain the object, the present invention is configured as follows.

In an automatic analysis apparatus and a sample measuring method: the operations of a sample dispensing mechanism to intake and discharge a sample to a reaction container and a reagent dispensing mechanism to intake and discharge a reagent to the reaction container are controlled; the allowable concentration range of a calibration curve is set for each of a plurality of photometers to detect the light projected to the reaction container; one of the plural photometers is selected in accordance with the concentration of the sample computed on the basis of the light detected with each of the plural photometers in the set allowable concentration range; and the concentration based on the light detected with the selected photometer is decided as the concentration of the sample.

Effects of Invention

The present invention makes it possible to materialize an automatic analysis apparatus and a sample measuring method, which are capable of: deciding an optimum photometer from the two photometers of a light-scattering photometer and an absorptiometer in accordance with a concentration range; and improving detection sensitivity.

BRIEF DESCRIPTION OF DRAWINGS

FIG. 15 is an example of a screen of an operation section in an example according to the present invention.

FIG. 16 is an example of a screen of an operation section in an example according to the present invention.

MODE FOR CARRYING OUT THE INVENTION

Embodiments according to the present invention are explained hereunder in reference to the attached drawings.

Embodiment 1

Prior to explanations on examples according to the present invention, immune reaction and antigen-antibody reaction are explained.

In antigen-antibody binding reaction, the reaction to an antigen advances relatively slowly. It is possible to monitor a reaction process by measuring an absorbance and scattered light at intervals of several seconds since the reaction time is a level of several minutes.

An absorptiometer measures an absorbance on the basis of the relative relationship of the quantity of the light having penetrated a solution to irradiated light, namely the Lambert-Beer Law, as shown in the following expression (1).

[Num-1]

$$\text{Abs} = -\log\frac{I_S}{I_{100}} \quad \text{Expression (1)}$$

A light-scattering photometer is based on the fact that scattered light does not exist and nearly "zero" in the case of using water as a reaction solution and the scattered light increases as an antigen-antibody reactant increases.

In general, a scattered light quantity of particles is described by the following expression (2) when the scattering is regard mostly as Rayleigh scattering.

[Num-2]

$$\frac{I}{I_0} = \frac{8\pi^4 n\alpha}{\lambda^4 \gamma^2}(1+\cos^2\theta)V \quad \text{Expression (2)}$$

Here, n represents the number of particles per 1 $cm^3$, V represents a total scattering volume, α represents a polarizability of particles, and λ represents a wavelength.

Figure 5:
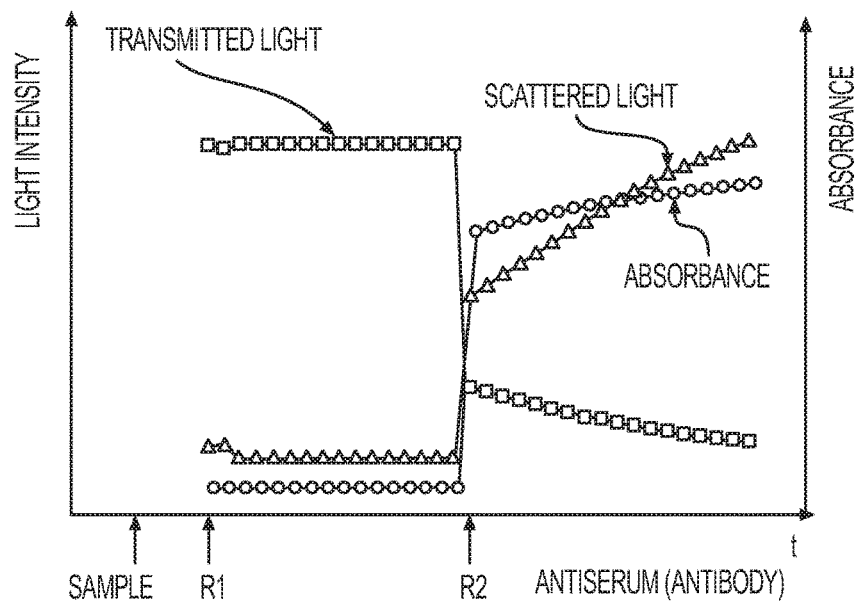
FIG. 5 is a view showing the relationship of reaction among transmitted light, scattered light, and an absorbance.

FIG. 5 is a view showing the relationship of reaction among transmitted light, scattered light, and an absorbance, and the vertical axis represents a light intensity and the horizontal axis represents time. As shown in FIG. 5, the transmitted light (quadrangles) reduces in proportion to the progress of reaction and the scattered light (triangles) increases in proportion to the progress of reaction. Further, the absorbance (circles) increases in proportion to the progress of reaction.

In the region of clinical examination, the detection limit and the quantification limit of a measuring method have important implications from a clinical viewpoint in the measurement of the concentration of a tumor marker or the like. The detection limit: means the smallest detectable quantity of a measurement object substance existing in a sample; and is not necessarily a quantifiable limit. The detection limit is obtained by a method of: repeatedly measuring a blind sample and actual samples of known low concentrations (5 or more kinds of dilution series); and reading the measured value of the sample in which for example the average value of the blind sample+3SD and the average value of the low concentration sample−3SD do not overlap with each other. That is, the detection limit is obtained by measuring a sample the concentration of which is known and measuring a signal quantity (sensitivity) with a photometer.

In contrast, the method of computing the concentration of a general patient sample is a method of firstly measuring standard solutions of known concentrations at plural points, thus making a calibration curve, successively measuring the sample, and obtaining a concentration corresponding to a signal quantity from the calibration curve on the basis of the signal quantity detected with a photometer.

In immunoserological test, an antigen contained in blood serum or blood plasma is reacted with a reagent containing an antibody corresponding to the antigen and an antigen-antibody product is produced. A concentration is computed from the absorbance change or the scattered light change of the antigen-antibody product.

As measuring methods, there are a measuring method of using transmitted light and a measuring method of using scattered light. By the scattered light measurement, it is possible to detect a minute change of antigen-antibody reaction. As a result, the detection limit at a lower concentration improves.

In the case of a sample having a high antigen concentration in contrast, the quantity of an antigen-antibody product is large, scattered light increases scarcely in a high concentration region, and the range of a straight line is narrow.

In immunoserological test, the influence by immunity, bilirubin, turbidity by lipid, hemolysis caused by the fragmentation of erythrocytes, and others which are contained in a sample of a patient is included.

The present invention is created on the basis of the above matters.

Example 1 according to the present invention is explained hereunder.

In Example 1 according to the present invention, a plurality of photometers (a light-scattering photometer and an absorptiometer) are arranged along the circumference of a reaction disk. That is, an immune nephelometer (light-scattering photometer) and an absorptiometer, those being operated with the plural devices of different analysis principles, are mounted on an automatic analysis apparatus for biochemistry.

Figure 1:
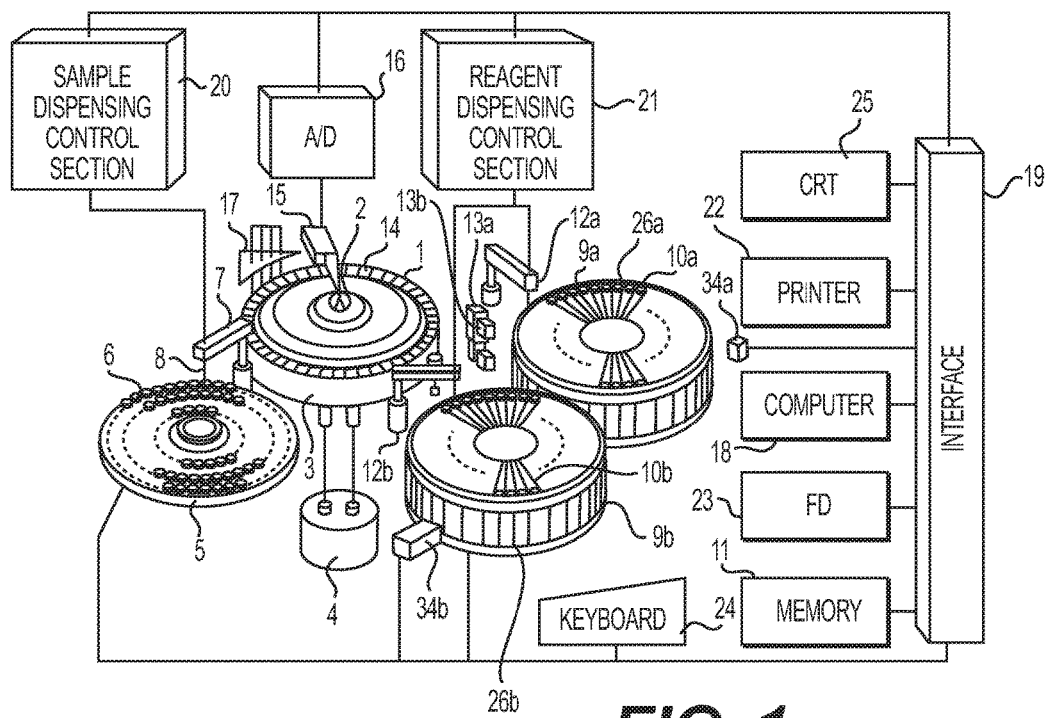
FIG. 1 is a schematic general configuration diagram of an automatic analysis apparatus to which an example according to the present invention is applied.

FIG. 1 is a schematic general configuration diagram of an automatic analysis apparatus to which Example 1 according to the present invention is applied. In FIG. 1, many reaction containers 2 comprising a translucent material are mounted on and along the circumference of a reaction disk 1 intermittently rotatably installed. The reaction containers 2 are maintained at a given temperature (37 degrees C. for example) by a constant-temperature bath 3. The temperature of a fluid in the constant-temperature bath 3 is controlled by a constant-temperature retainer 4.

Many sample containers 6 containing biological samples such as blood or urine are arranged over a sample disk 5. A pipet nozzle 8 attached to a movable arm 7 intakes a given quantity of a sample from a sample container 6 allocated at the intake position of the sample disk 5 and discharges the sample in a reaction container 2 located at the discharge position over the reaction disk 1.

A plurality of reagent bottles 10A and 10B to which labels showing reagent identification information such as barcodes are attached are arranged over reagent disks 26A and 26B arranged in reagent cool boxes 9A and 9B, respectively. Reagent liquids corresponding to analysis items that can be analyzed by the automatic analysis apparatus are contained in the reagent bottles 10A and 10B.

Barcode readers 34A and 34B pertaining to the respective reagent cool boxes 9A and 9B read the barcodes displayed on the outer walls of the reagent bottles 10A and 10B when reagents are registered. The read reagent information is registered in a memory 11 that will be described later, together with the information on the positions over the reagent disks 26A and 26B.

Reagent pipet nozzles in respective reagent dispensing mechanisms 12A and 12B: intake reagent liquids from the reagent bottles 10A and 10B corresponding to the examination items allocated at reagent receiving positions over the reaction disk 1; and discharge the reagent liquids to the relevant reaction containers 2. The mixtures of the samples and the reagents contained in the reaction containers 2 are stirred with stirring mechanisms 13A and 13B. The array of the reaction containers 2 moves rotatably so as to pass through photometric positions interposed between light sources 14 (light sources 14A and 14B) and photometers 15 (a light-scattering photometer 15A and a multi-wavelength absorptiometer 15B). The photometers 15 can compute concentrations by using both scattered light and transmitted light. Here, the placement of the detectors in the photometers 15 is described later in reference to FIGS. 2 and 3.

The reaction liquid of the sample and the reagent in each of the reaction containers 2 is photometrically measured during the rotary operation of the reaction disk 1 every time when the reaction liquid intersects the front of the photometers 15. Each of the samples is measured with the photometers 15 and the outputted analog signals are inputted in an A/D converter 16. A reaction container cleaning mechanism 17 arranged in the vicinity of the reaction disk 1 makes it possible to use the reaction containers 2 repeatedly by cleaning the interior of a used reaction container 2.

Successively, a control system and a signal processing system in an automatic analysis apparatus shown in FIG. 1 are explained briefly.

A computer 18 is connected to a sample dispensing control section 20, a reagent dispensing control section 21, and the A/D converter 16 through an interface 19. The computer 18 sends a command to the sample dispensing control section 20 and controls the dispensing operation of a sample. Further, the computer 18 sends a command to the reagent dispensing control section 21 and controls the dispensing operation of a reagent.

The analog signals outputted from the photometers 15 are converted to digital signals with the A/D converter 16 and taken in the computer 18.

A printer 22 for printing, a memory 11 and an external output medium 23 as storage devices, a keyboard 24 for inputting operation commands and the like, and a CRT display 25 for displaying a screen are connected to the interface 19. As a screen display device, in addition to a CRT display, a liquid crystal display or the like can be adopted.

The memory 11 comprises a hard disk memory or an external memory for example. In the memory 11, information on the password of each operator, the display level of each screen, analysis parameters, the requested contents of analysis items, calibration results, analysis results, etc. is stored.

Successively, the analytical operations of a sample in the automatic analysis apparatus shown in FIG. 1 are explained. Analysis parameters related to items analyzable with the automatic analysis apparatus are inputted through an information input device like the keyboard 24 beforehand and stored in the memory 11. An operator selects examination items required of each sample by using an operational function screen that will be described later.

On this occasion, information such as a patient ID is also inputted from the keyboard 24. In order to analyze an examination item indicated to each sample, the pipet nozzle 8 dispenses a given quantity of a sample from a sample container 6 to a reaction container 2 in accordance with an analysis parameter.

The reaction container 2 having received the sample is transferred by the rotation of the reaction disk 1 and stops at a reagent receiving position. A pipet nozzle of a reagent dispensing mechanism 12A or 12B dispenses a given quantity of a reagent liquid to the reaction container 2 in accordance with the analysis parameter of the relevant examination item. With regard to the sequence of dispensing a sample and a reagent, inversely to the above case, a reagent may be dispensed in advance of a sample.

Successively, the sample and the reagent are stirred and mixed with a stirring mechanism 13A or 13B. When the sample and the reagent are stirred and the reaction container 2 intersects a photometric position, the scattered light or the absorbance of the reaction liquid is photometrically measured with the photometers 15. The photometrically measured scattered light or the like is converted to a numerical value proportional to a light quantity or the like with the A/D converter 16 and taken into the computer 18 through the interface 19. The converted numerical value is converted to a concentration datum on the basis of a calibration curve measured beforehand by an analysis method designated to each examination item. An ingredient concentration datum as an analysis result of each examination item is outputted to the printer 22 or on the screen of the CRT 25.

In advance of the implementation of the measurement operations, an operator carries out the setting of various parameters and the registration of a sample required for analytical measurement through the operation screen of the CRT 25. Further, the operator checks the analysis result after the measurement on the operation screen of the CRT 25.

Figure 2:
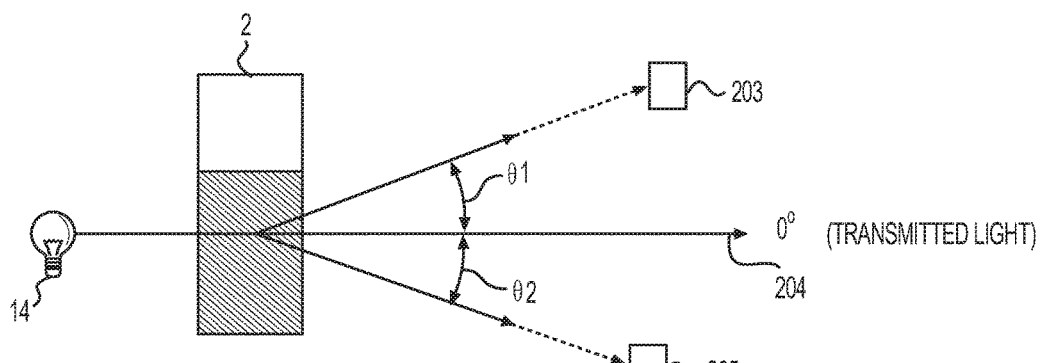
FIG. 2 is a view explaining the arrangement of a light source, a reaction container, and a light-scattering photometer 15 in an example according to the present invention.
Figure 3:
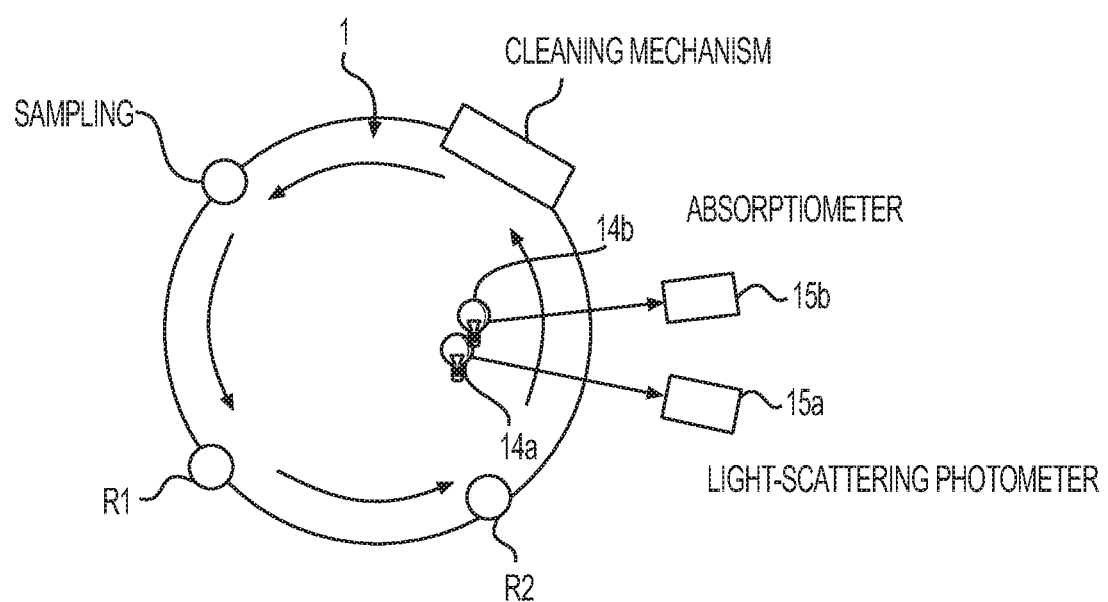
FIG. 3 is a schematic top view of a reaction disk in an example according to the present invention.

Successively, the arrangement of a light source 14 and a photometer 15 shown in FIG. 1 is explained in reference to FIGS. 2 and 3.

FIG. 2 is a view explaining the arrangement of a light source 14, a reaction container 2, and a light-scattering photometer 15A (detectors 203, 204, and 205).

The light emitted from the light source 14 is projected to the reaction container 2 in which a measurement object is dispensed. The incident light collides with the measurement object and is scattered in the reaction container 2. With regard to the scattered light, in the case of FIG. 2, the detector 203 is arranged at a position forming an angle of θ1 with the light coming from the light source 14 and having passed through the reaction container 2 in the vertical direction (Z-axis direction) of the apparatus. Further, the detector 204 is arranged in the direction (angle zero) of the light coming from the light source 14 and having passed through the reaction container 2. Furthermore, the detector 205 is arranged at a position forming an angle of θ2 with the light coming from the light source 14 and having passed through the reaction container 2 in the vertical direction (Z-axis direction) of the apparatus.

Although the detectors 203, 204, and 205 are allocated in the Z-axis direction to the incident light, it is also possible to be allocated by changing the angles to the horizontal direction (X-axis and Y-axis directions) of the apparatus. Further, the detectors 203, 204, and 205 are not necessarily allocated discretely but may be allocated continuously.

FIG. 3 is a schematic top view of the reaction disk 1 and shows arrangement positions of the light-scattering photometer 15A and the absorptiometer 15B. In the automatic analysis apparatus configured as shown in FIG. 1, the light-scattering photometer 15A and the absorptiometer 15B are aligned on the lines where the light from the light sources 14A and 14B passes through a reaction container 2.

Each analysis item of a sample is measured simultaneously with the light-scattering photometer 15A and the absorptiometer 15B and the reaction process is made measurable. It is important that the light-scattering photometer 15A and the absorptiometer 15B can measure nearly simultaneously. The setting contents of analysis parameters, concentration computation, and data abnormality detection by an interference substance in a sample in the light-scattering photometer 15A and the absorptiometer 15B are explained hereunder.

A reagent quantity and a sample quantity in the analysis parameters are used commonly by the light-scattering photometer 15A and the absorptiometer 15B and, with regard to other items including wavelength selection, a measurement point, alarm setting, and a calibration condition, the parameters are used independently between the photometers 15A and 15B.

The procedure of the calibration, concentration, data check, and alarm generation of the absorptiometer 15B and the light-scattering photometer 15A is described. The data flow is represented by the following procedure. The procedure is (1) parameter setting, (2) calibration parameter computation, (3) concentration computation, (4) concentration judgment logic, and (5) interference substance check and they are explained in sequence.

(1) Parameter Setting

The measurement parameters of a plurality of optical systems are made settable for each item. Table 2 is a list of the parameters.

TABLE 2

| Parameter list | | |
|---|---|---|
| | Absorptiometer | Light-scattering photometer |
| Common parameter | | |
| Item name | | AFP |
| Type | | Serum |
| Sample quantity | | 1.0-30.0 μL |
| Reagent quantity (R1) | | 10-150 μL |
| Reagent quantity (R2) | | 10-150 μL |
| Reagent quantity (R3) | | 10-150 μL |

TABLE 2-continued

Parameter list

| | Absorptiometer | Light-scattering photometer |
|---|---|---|
| Individual parameter | | |
| Wavelength | 340-800 nm selection | Angle selection 0°/±20°/±30° To retain data for each angle |
| Photometric point | 19-34 points | 19-34 points |
| Analysis method | End point/2 points/rate selection | End point/2 points/rate selection |
| Calibration method | Linear/Non-Linear | Linear/Non- Linear |
| Calibration point number | 6 points | 6 points |
| Mutual parameter | | |
| Linearity (concentration range) | | Range setting of low/middle/high concentrations |
| Linearity (Concentration conversion) | | To select absorptiometer/light-scattering photometer according to low/middle/high concentrations |
| Coexisting material | | |
| L (Turbidity) | | To designate check value according to low/middle/high concentrations |
| H (Hemolysis) | | To designate check value according to low/middle/high concentrations |
| I (Yellow) | | To designate check value according to low/middle/high concentrations |
| Alarm check | | |
| Convergence allowable absorbance/scattered light intensity | Range designation | Range designation |
| Variation allowable absorbance/scattered light intensity | Range designation | Range designation |
| Sensitivity allowable absorbance/scattered light intensity | Range designation | Range designation |
| First standard solution absorbance/scattered light intensity range | Range designation | Range designation Range designation Range designation |
| Linearity check Prozone limit value | Range designation | |
| Reaction limit absorbance/scattered light intensity | Range designation Range designation | |

Common parameters (a sample quantity and a reagent quantity) ranging over the plural optical systems, intrinsic parameters specific to the respective photometers 15A and 15B, mutual parameters of a concentration from data related to the plural photometers 15A and 15B, and parameters for alarm check, those being shown in Table 2, are stored in a database.

Figure 4:
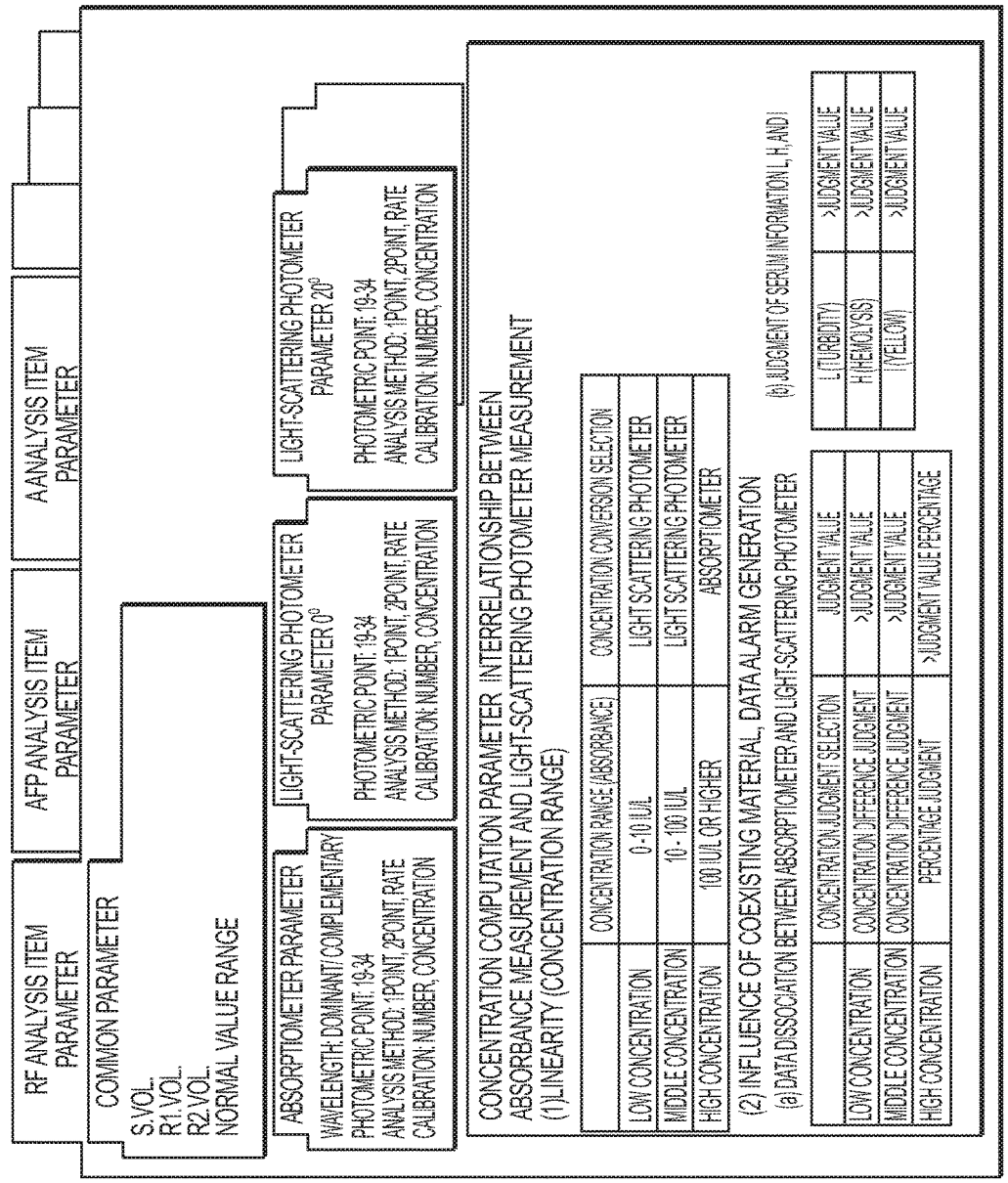
FIG. 4 is a view showing the database configuration of parameters in each of the items in an example according to the present invention.

FIG. 4 is a view showing the database configuration of common parameters, parameters dedicated to an absorptiometer, parameters dedicated to a light-scattering photometer, concentration computation parameters, and coexisting material check parameters for each item.

(a) Common Parameters

Parameters, such as a sample quantity, a dispensing reagent quantity, and a normal value range, related to quantity are set.

(b) Parameters Dedicated to Absorptiometer

Parameters, such as a wave length (dominant wavelength/complementary wavelength), an analysis method (1 point, 2 points, Rate), a photometric point, and calibration (number and concentration), used for computation in an absorptiometric method are set.

(c) Parameters Dedicated to Light-Scattering Photometer

An angle is selected from among 0 degree, ±10 degrees, ±20 degrees, and ±30 degrees for example. The parameters are the parameters, such as an analysis method (1 point, 2 points, Rate), a photometric point, and calibration (number and concentration), used for computation in a light-scattering photometric method and are set for each scattering angle.

(d) Concentration Computation Parameters

The parameters are the parameters related to interrelationship between absorbance measurement and light-scattering photometer measurement and the parameters of linearity and coexisting material check are set.

When sensitivity is compared between a plurality of optical systems, between a light-scattering photometer 15A and an absorptiometer 15B for example, the signals are different and hence a sensitivity per unit concentration cannot simply be compared. In the optical measurement of latex particles or the like, the scattering of light is measured in the blank state of a latex particle solution even in an unreacted state. Further, with the absorptiometer 15B, scattering occurs and hence a large absorbance value is measured. When a blank solution of latex is measured with the light-scattering photometer 15A, the scattered light reduces comparatively.

The relationship of latex particles is described by the following items (1-1) to (1-4).

(1-1) A measurement result varies in accordance with the conditions of a latex particle diameter, the number of particles per unit volume, and an irradiation wavelength.

(1-2) The magnitude of scattered light is largely different between a latex single body and a latex body formed after an antibody has reacted with an antigen on the surface of the latex.

(1-3) In general, also the affinity between an antibody and an antigen has a large influence.

(1-4) The relationship of sensitivity between scattered light and an absorbance in the case where the concentration of an antigen is high is largely different from the case of a low concentration.

Successively, linearity and coexisting material check parameters are explained.

(I) Linearity (Allowable Range Setting in Each Calibration)

A concentration range, for example, may be divided into three levels of low concentration, middle concentration, and high concentration from a curve of calibration with an absorptiometer 15B or may be divided in accordance with the concentrations of each standard solution.

In order to set a concentration computation method used in each concentration range, it is necessary to decide a signal (photometer) used in each region from calibration result. In deciding the parameter of linearity, the following three items (a), (b), and (c) are retained.

(a) To input a concentration range decided from a relevant reagent lot by experiment or the like beforehand.

(b) To decide a concentration range usable in each optical system from the measurement result of a plurality of optical systems, the sensitivity of a reagent, and the like and set the range automatically.

(c) An allowable range can be inputted arbitrarily by an operator. It can be set manually.

In the item (a), for example a reagent maker decides a concentration range for each reagent lot and provides the information to a user. In the item (b), the sensitivity of the light-scattering photometer 15A is obtained in terms of a light quantity change ratio in order to compare the sensitivity between the light-scattering photometer 15A and the absorptiometer 15B. The light quantity change ratio is a value obtained by subtracting a base light quantity immediately after a second reagent is added from the variation of a light quantity changed between before and after reaction and the scattering of light in a blank state can be disregarded.

The sensitivities of the light-scattering photometer 15A and the absorptiometer 15B ranging from a low concentration to a high concentration are different largely also in accordance with a reagent lot and an analysis item. It comes to be important for a system comprising a plurality of photometers to carry out measurement with an optimum optical system in each of the concentration regions ranging from a low concentration to a high concentration.

The workflow (b) to judge an optimum photometer from a photometer A and a photometer B is explained hereunder on the basis of a certain standard value.

Here, the standard sensitivity A of the photometer A is set at 0.001 and the standard sensitivity B of the photometer B is set at 0.002. When calibration is carried out with a certain reagent lot, the calibration result A is 0.002 and the calibration result B is 0.005. If the calibration results are compared with the standard sensitivities, the sensitivity of the photometer A increases by 2 times, the sensitivity of the photometer B increases by 2.5 times, and on this occasion the photometer B of a higher sensitivity is selected.

(II) Coexisting Material Check Parameters

When data dissociation occurs between an absorptiometer 15B and a light-scattering photometer 15A, a value for judging that the data dissociate between the absorptiometer 15B and the light-scattering photometer 15A is set.

Figure 12:
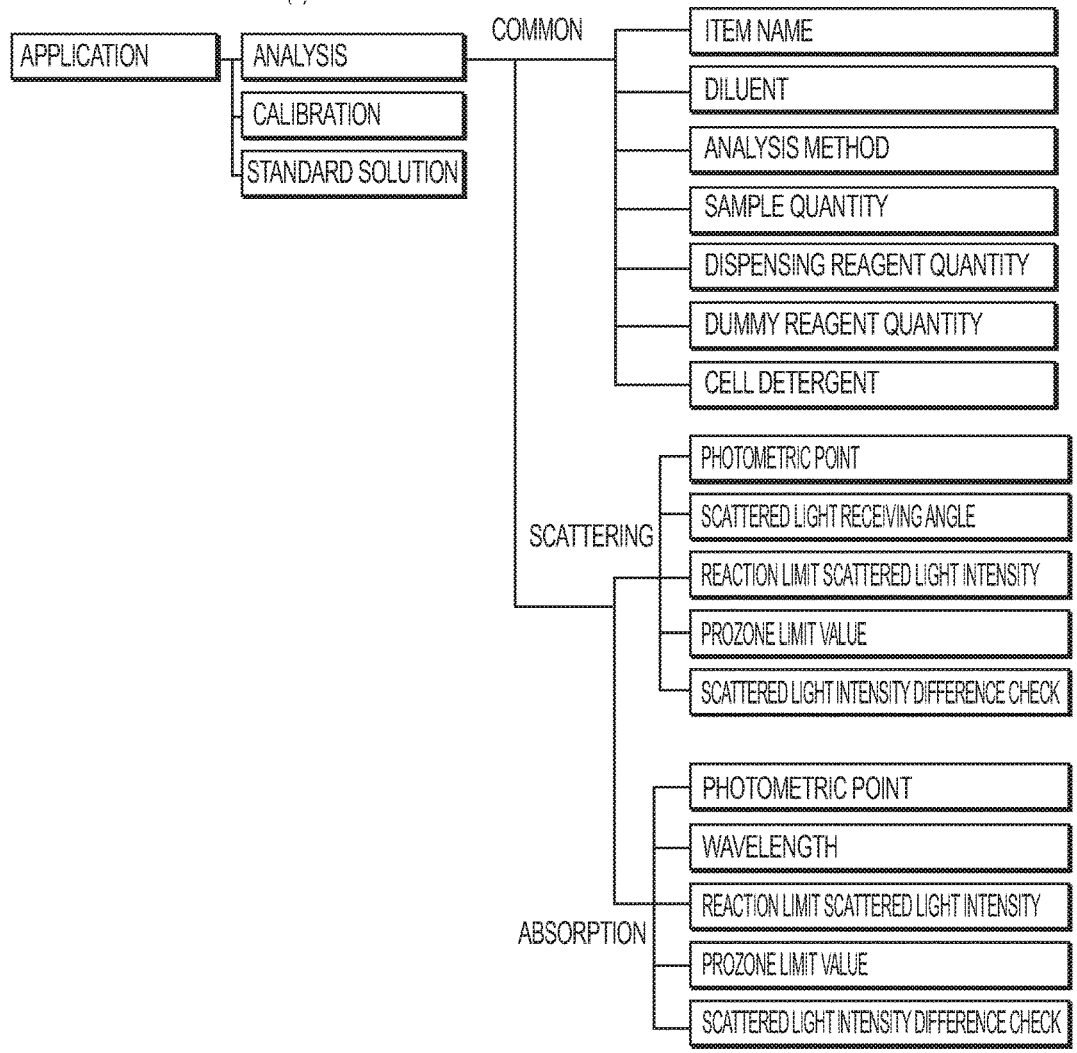
FIG. 12 is a screen configuration diagram of an operation section in an example according to the present invention.
Figure 13:
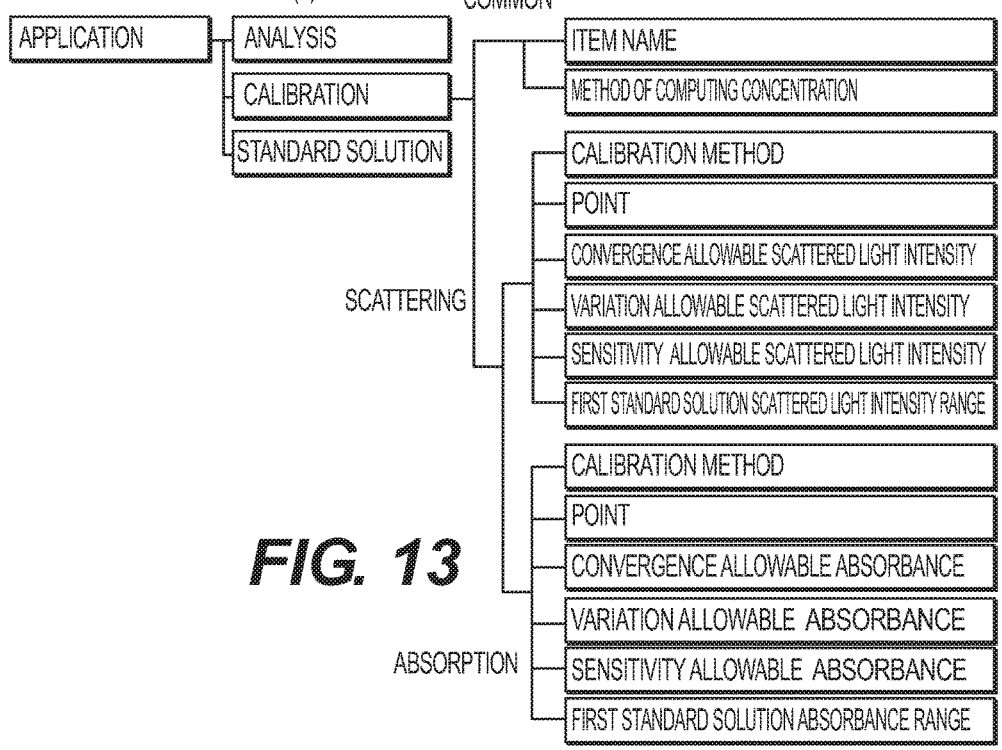
FIG. 13 is a screen configuration diagram of an operation section in an example according to the present invention.
Figure 14:
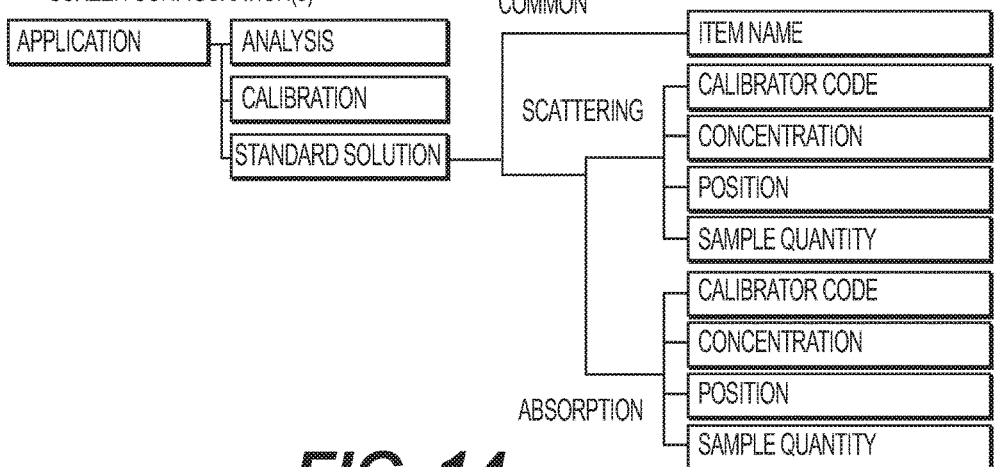
FIG. 14 is a screen configuration diagram of an operation section in an example according to the present invention.
Figure 17:
FIG. 17 is an example of a screen of an operation section in an example according to the present invention.

Screen configuration diagrams of an operation section in the aforementioned parameter setting are shown in FIGS. 12 to 14 and screen examples of the operation section are shown in FIGS. 15 to 17.

That is, as shown in FIGS. 12 to 14, in application setting, there are three items of analysis, calibration, and a standard solution, and FIG. 12 shows the setting items of analysis, FIG. 13 shows the setting items of calibration, and FIG. 14 shows the setting items of a standard solution.

As shown in FIG. 12, in the analysis, there are common items, items on a light-scattering photometer, and items on an absorptiometer and, in the common items, there are an item name, a diluent, an analysis method, a sample quantity, a dispensing reagent quantity, a dummy reagent quantity, and a cell detergent. Further, in the items on a light-scattering photometer, there are a photometric point, a scattered light receiving angle, a reaction limit scattered light intensity, a prozone limit value, and scattered light intensity difference check. Furthermore, in the items on an absorptiometer, there are a photometric point, a wavelength, a reaction limit scattered light intensity, a prozone limit value, and scattered light intensity difference check.

FIG. 15 is a view showing an example of a setting screen 25A on analysis. Analysis is selected from the three items of analysis, calibration, and a standard solution. In the example of FIG. 15, IRI is selected as the item name and selections on a sample quantity, a dispensing reagent quantity, a dummy reagent quantity, and a cell detergent, selections on an analysis method, a photometric point, and a wavelength of an absorptiometer, and selections on an analysis method, a photometric point, and a light receiving angle of a light-scattering photometer are carried out.

Further, as shown in FIG. 13, in calibration, there are common items, items on a light-scattering photometer, and items on an absorptiometer and, in the common items, there are an item name and a concentration computation method. Further, in the items of a light-scattering photometer, there are a calibration method, a point, a convergence allowable scattered light intensity, a variation allowable scattered light intensity, a sensitivity allowable scattered light intensity, and a first standard solution scattered light intensity range. Furthermore, in the items on an absorptiometer, there are a calibration method, a point, a convergence allowable absorbance, a variation allowable absorbance, a sensitivity allowable absorbance, and a first standard solution absorbance range.

FIG. 16 is a view showing an example of a setting screen 25B on calibration. Calibration is selected from the three items of analysis, calibration, and a standard solution. In the example of FIG. 16, IRI is selected as the item name and automation is selected as a concentration computation method. Then selections on a calibration method, a point, a convergence allowable absorbance, a variation allowable absorbance, a sensitivity allowable absorbance, and a first standard solution absorbance range of an absorptiometer are carried out and further selections on a calibration method, a point, a convergence allowable scattered light intensity, a variation allowable scattered light intensity, a sensitivity allowable scattered light intensity, and a first standard solution scattered light intensity range of a light-scattering photometer are carried out.

Further, as shown in FIG. 14, in a standard solution, there are a common item, items on a light-scattering photometer, and items on an absorptiometer and, in the common item, there is an item name and, in the items on the light-scattering photometer and the absorptiometer, there are a calibrator code, a concentration, a position, and a sample quantity, respectively.

FIG. 17 is a view showing an example of a setting screen 25C on a standard solution. A standard solution is selected from the three items of analysis, calibration, and the standard solution. In the example of FIG. 17, IRI is selected as the item name and selections on a calibrator code, a standard solution concentration, a position, and a sample quantity are carried out in each of an absorptiometer and a light-scattering photometer.

(2) Calibration Parameter Computation

The measurement of a blank solution and a standard solution is carried out and calibration parameters are computed. Calibration parameters of both the absorptiometric method and the light-scattering photometer are computed. When computations are carried out at scattering angles of 20 and 30 degrees and by the absorptiometric method, three kinds of K factors are obtained through the expressions (3) to (5).

In the absorptiometric method, when a blank is represented by S1Abs, a blank concentration by Conc.B, an absorbance of a standard solution by $Abs_S$, and a standard solution concentration by Conc.S, a factor K is computed through the following expression (3).

[Num-3]

$$K = \frac{Conc.\ S - Conc.\ B}{Abs_S - S1Abs} \quad \text{Expression (3)}$$

At a scattering angle of 20 degrees in the light-scattering photometer, when a blank is represented by $I_{B20}$, a blank concentration by Conc.B, a standard solution by $I_{S20}$, and a standard solution concentration by Conc.S, a factor $K_{20}$ is computed through the following expression (4).

[Num-4]

$$K_{20} = \frac{Conc.\ S - Conc.\ B}{I_{S20} - I_{B20}} \quad \text{Expression (4)}$$

At a scattering angle of 30 degrees in the light-scattering photometer, when a blank is represented by $I_{B30}$, a blank concentration by Conc.B, a standard solution by $I_{S30}$, and a standard solution concentration by Conc.S, a factor $K_{30}$ is computed through the following expression (5).

[Num-5]

$$K_{20} = \frac{Conc.\ S - Conc.\ B}{I_{S30} - I_{B30}} \quad \text{Expression (5)}$$

The calibration parameters are stored in a database such as a memory 11.

When calibration is carried out with an approximate curve by using a multipoint calibration curve and a plurality of standard solutions, in the absorptiometric method, A, B, and C parameters are stored in addition to S1ABS and K. In the light-scattering photometer, A, B, and C parameters are stored in addition to $I_B$ and K.

(3) Measurement and Concentration Computation of General Sample

A calibration curve is created individually for each of the optical systems of the absorptiometric method and the light-scattering photometer.

Concentration conversion for a patient sample is carried out with a plurality of calibration curves. The concentration conversion formulae are shown hereunder. Concentrations are computed for both the cases of the absorbance and the light-scattering photometer. When the concentrations are computed at the scattering angles of 20 and 30 degrees and with the absorptiometer, three kinds of concentrations are obtained through the expressions (6) to (8).

In the case of the absorptiometer, a concentration $Conc_{Abs}$ is obtained through the following expression (6).

[Num-6]

$$Conc_{Abs} = K_{Abs}(ABs_s - S1Abs) \quad \text{Expression (6)}$$

In the case of the light-scattering photometer, concentrations $Conc_{20N}$ and $Conc_{30N}$ are obtained through the following expressions (7) and (8).

[Num-7]

$$Conc_{20N} = K_{20}(I_{s20} - I_{B20}) \quad \text{Expression (7)}$$

[Num-8]

$$Conc_{30N} = K_{30}(I_{s30} - I_{B30}) \quad \text{Expression (8)}$$

Table 3 shows the measurement results of an RF in the cases of computing the concentrations at the scattering angles of 20 and 30 degrees and with the absorptiometer.

TABLE 3

| | RF measurement result when concentrations are computed with light-scattering photometer and absorptiometer | | |
|---|---|---|---|
| Concentration region | Absorbance | Light-scattering photometer | |
| IU/mL | $Conc._{Abs}$ | $Conc._{20N}$ | $Conc._{30N}$ |
| Low concentration | 1.7 | 0.3 | 0.3 |
| Middle concentration (normal region) | 8.8 | 10.0 | 10.0 |
| High concentration | 310.0 | 173.4 | 116.5 |

(4) Concentration Judgment Logic

Figure 6:
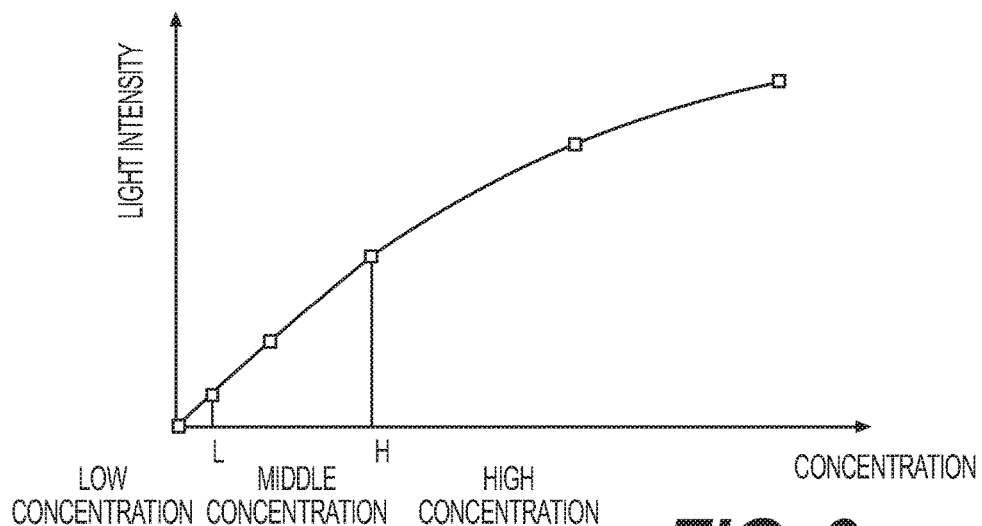
FIG. 6 is a graph showing the relationship among an absorbance, a scattering intensity, and a concentration in an RF.
Figure 7:
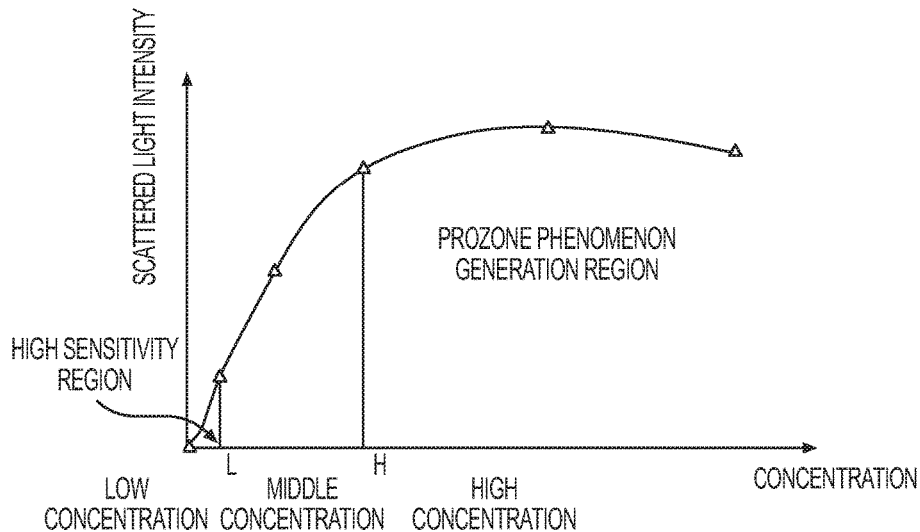
FIG. 7 is a graph showing the relationship among an absorbance, a scattering intensity, and a concentration in an RF.

FIGS. 6 and 7 are the graphs showing the relationships between an absorbance/a scattering intensity and a concentration in an RF. As shown in FIG. 7, in the light-scattering photometer, the signal reduces at a high concentration. Consequently, even in the case of a sample originally having a high concentration, the concentration is equivalent to an absorbance of a middle concentration and may possibly be displayed as a low concentration.

In contrast, as shown in FIG. 6, in the case of the absorptiometer, even at a high concentration, the absorbance does not reduce and is higher than that of a middle concentration.

In the low concentration region, the sensitivity of the light-scattering photometer is better than that of the absorptiometer. In the case of the light-scattering photometer, a prozone phenomenon is caused at the high concentration region. It sometimes happens that a scattered light intensity comes to be equivalent to a scattering intensity of a lower concentration in despite of a high concentration.

Figure 8:
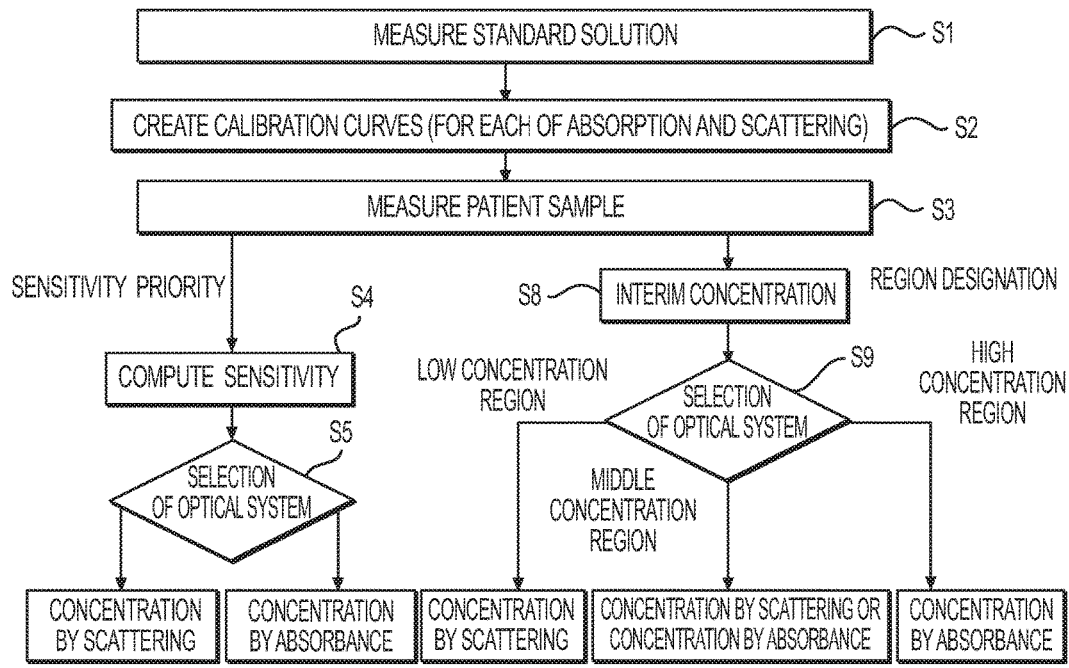
FIG. 8 is a view showing the flow of judging a concentration from a sensitivity or a concentration range and selecting a photometer in an example according to the present invention.

FIG. 8 is a view showing the flow of judging a concentration from a sensitivity or a concentration range and selecting a photometer. Further, FIG. 18 is a functional block diagram of a computer (controller) 18 and is a view related to the function of carrying out the flow shown in FIG. 8.

Figure 18:
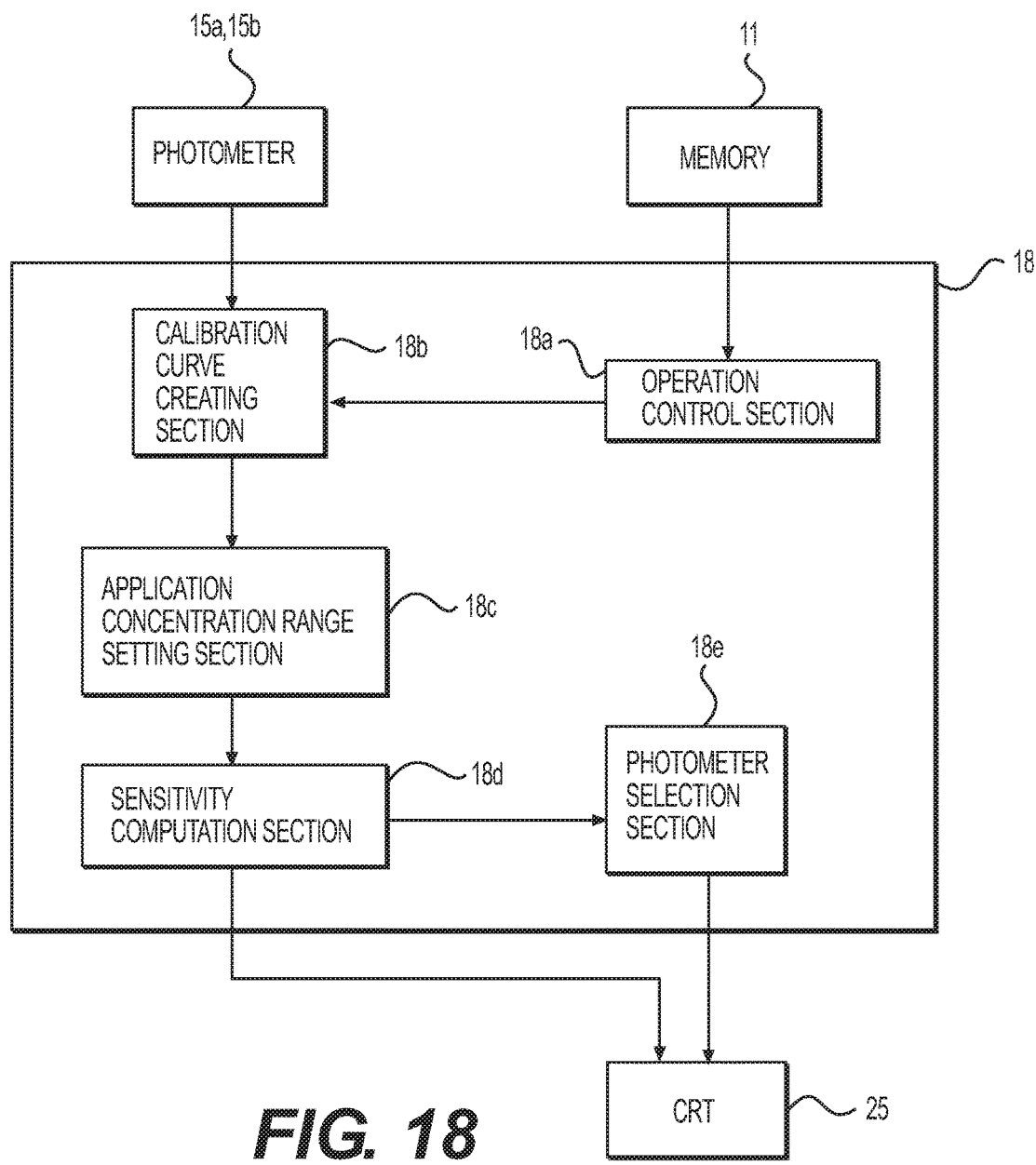
FIG. 18 is a functional block diagram of a computer (controller) in an example according to the present invention.

In FIG. 18, the computer (controller) 18 comprises: an operation control section 18a to control the operations of a reaction disk 1, photometers 15, and others; a calibration curve creating section 18b; an application concentration range setting section 18c; a sensitivity computation section 18d; and a photometer selection section 18e.

A concentration judgment flow shown in FIG. 8 to select a photometer by comparing sensitivities is explained in reference to FIGS. 8 and 18. The concentration judgment and photometer selection flow shown in FIG. 8 is carried out by the computer 18 controlling the operations of the sections and mechanisms of an automatic analysis apparatus on the basis of the parameters and the like stored in the memory 11.

In FIG. 8, in order to compare optical system sensitivities of different principles, the width of a concentration is computed from a calibration result. The procedure is as follows.

(4-1) The operation control section 18a and the calibration curve creating section 18b measure a standard solution multiple times by ordinary calibration and create a calibration curve (Step S1).

(4-2) The calibration curve creating section 18b creates the respective calibration curves of the absorptiometer and the light-scattering photometer from the measurement values of Min/Max of the concentrations of the respective standard solutions (Step S2).

(4-3) The application concentration range setting section 18c computes the upper/lower limits of the standard solution concentrations from the calibration curves of Min/Max (Step S3).

(4-4) The sensitivity computation section 18d computes sensitivities (signal quantities) from the data of the absorptiometer 15B and the light-scattering photometer 15A by using calibration parameters (Steps S3 and S4).

(4-5) The photometer computation section 18e decides the concentration to be used from a concentration by absorption and a concentration by scattered light on the basis of the sensitivities computed by the sensitivity computation section 18d (Step S5). That is, the computed sensitivities of the concentration by absorption and the concentration by scattered light are compared and the use of the concentration having a higher sensitivity is decided. The decided concentration is displayed on the CRT 25 (a concentration display section).

By the workflow shown in FIG. 8, it is possible to estimate a sensitivity from the maximum and the minimum obtained when the standard solution is measured multiple times and convert it to a concentration on the basis of the result. That is, the sensitivities of the respective optical systems (the absorptiometer and the light-scattering photometer) are computed as concentrations from the calibration results and hence the comparison between the sensitivity of the absorptiometer and the sensitivity of the light-scattering photometer can be facilitated.

The concentration range applied in the concentration judgment flow shown in FIG. 8 is explained.

Figure 9:
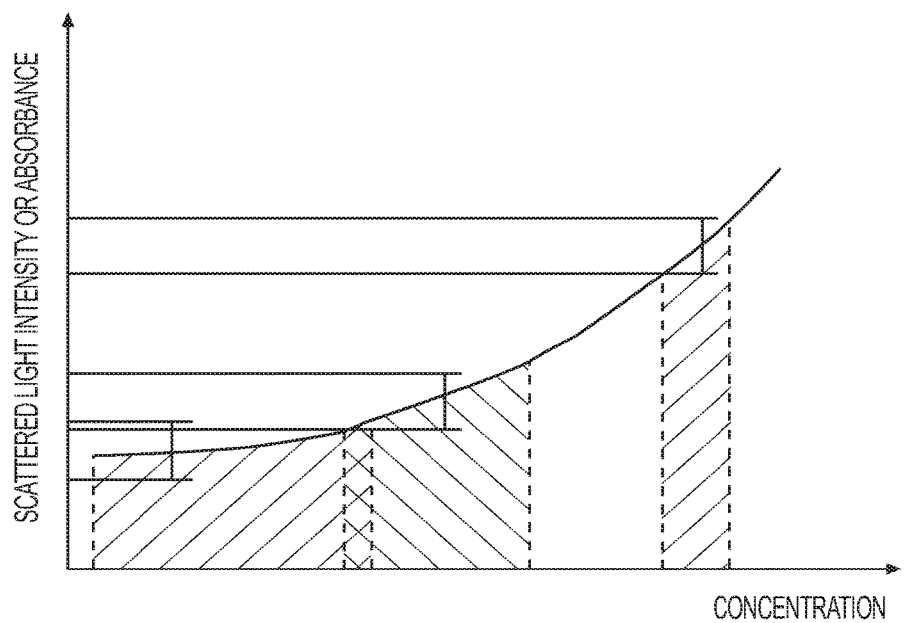
FIG. 9 is a graph showing the relationship between a scattered light intensity or an absorbance and a concentration.

A calibration curve varies in accordance with a concentration region in immune reaction. Consequently, verification and confirmation with respective standard solutions are required when calibration is carried out. For example, although the width of Min-Max is nearly constant in respective concentration regions in a reaction system in which a signal and a concentration are in the relationship of monotonic increase like enzyme reaction, in antigen-antibody reaction, as shown in FIG. 9, the sensitivity is low at a low concentration and hence the width of the concentration corresponding to a scattered light intensity or an absorbance is very wide. At a high concentration in contrast, it is obvious that the sensitivity is good because the width of Min/Max is small.

Here, the allowable concentration range of each standard solution can be set by either of the following two (a) and (b) methods, for example.

Figure 10A:
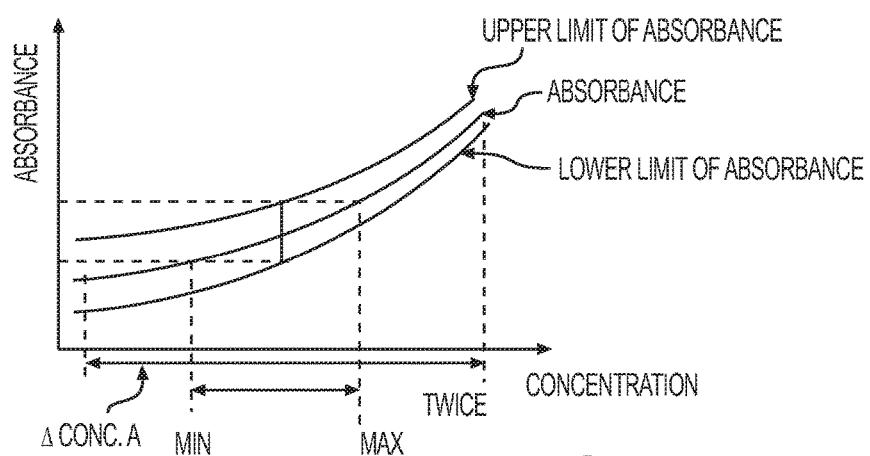
FIG. 10A is a graph showing an example of setting the allowable range of a calibration result from the double-width of Max/Min of the twice measurement result of each standard solution in an example according to the present invention.
Figure 10B:
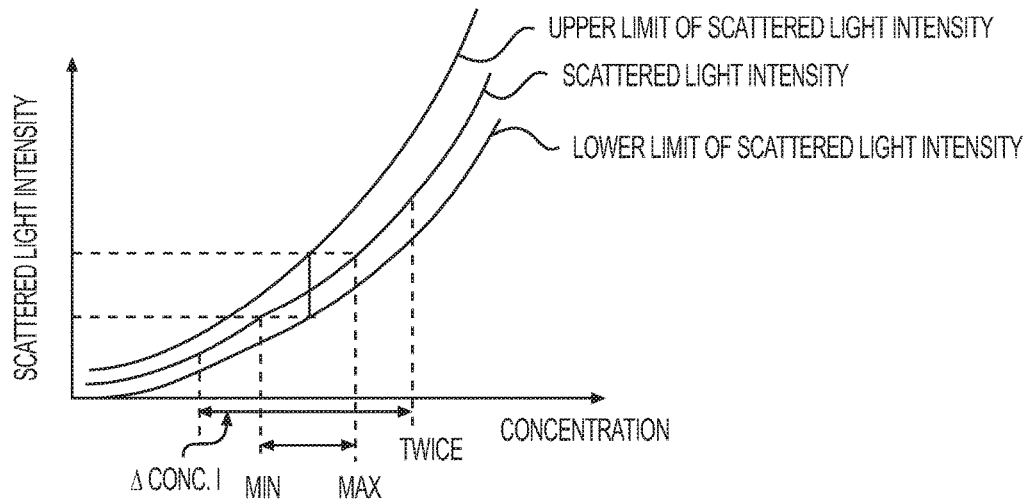
FIG. 10B is a graph showing an example of setting the allowable range of a calibration result from the double-width of Max/Min of the twice measurement result of each standard solution in an example according to the present invention.

(a) As shown in FIGS. 10A and 10B, the allowable range (calibration of Max/Min) of a calibration result is set from the double-width of Max/Min of the twice measurement result of each standard solution.

Figure 11:
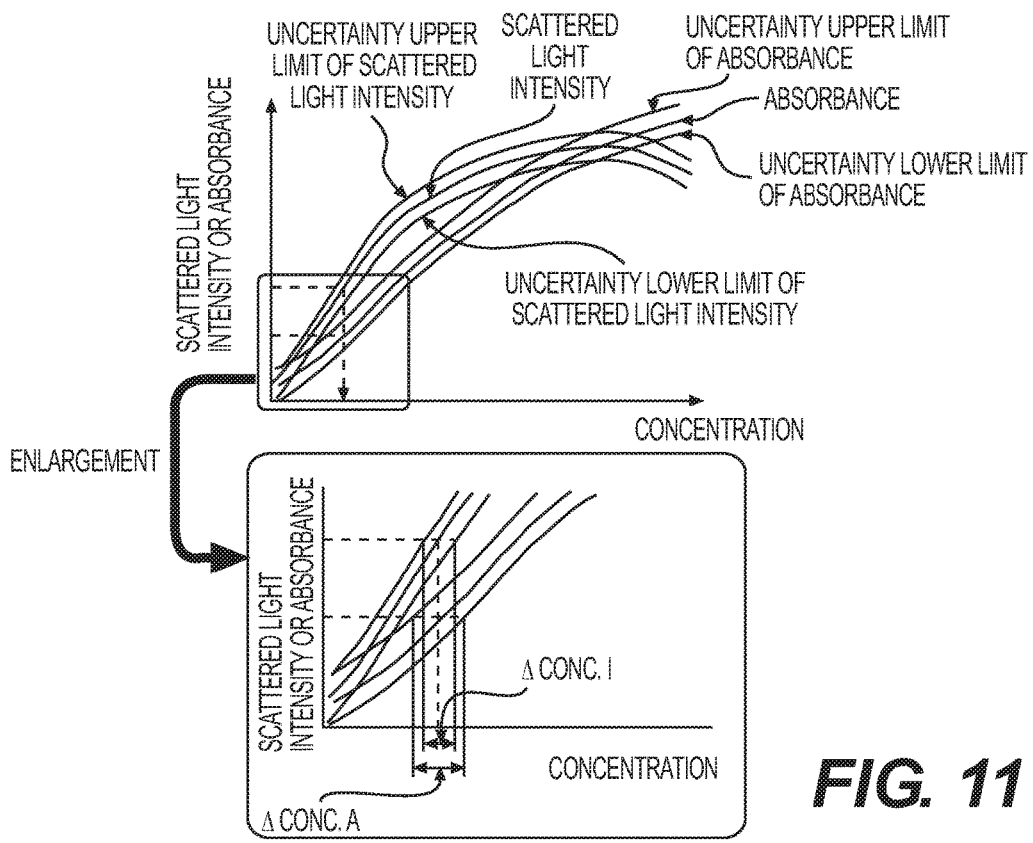
FIG. 11 is a view showing an example of setting the allowable range of calibration from uncertainty attached to a standard solution in an example according to the present invention.

(b) As shown in FIG. 11, the allowable range of calibration (calibration of Max/Min) is set as the variation of an optical system (photometer) from the uncertainty decided beforehand to a standard solution. With regard to the uncertainty, a signal is converted from the concentration range described in a document.

Then in the allowable concentration range obtained as stated above, the calibration curves are compared and the concentrations are computed from the calibration of the allowable ranges as stated below.

A calibration Abs of an absorbance is represented by $Conc._{Abs}$, a calibration AMax by $Conc._{Amax}$, and a calibration AMin by $Conc._{Amin}$.

Further, a calibration I of the light-scattering photometer is represented by $Conc._I$, a calibration IMax by $Conc._{IMax}$, and a calibration IMin by $Conc._{Imin}$ and then $Conc._{Amax}-Conc._{Amin}=$(delta) $Conc._A$ and $Conc._{Imax}-Conc._{Imin}=$(delta) $Conc._I$ are computed. That is, the concentration widths of the measured concentrations of the respective photometers are computed.

Then the computed (delta)$Conc._A$ and (delta)$Conc._I$ are compared and the one having a narrower allowable range when a concentration which the two calibration curves can take exists in a reliable interval is adopted. For example, in the case of (delta) $Conc._A>$(delta)$Conc._I$, $Conc._I$ is adopted as the reported value. That is, the measurement value by the light-scattering photometer is selected.

Then the measurement result in which the dispersion of the concentration is small (the measurement result of the light-scattering photometer in the above example) in the measurement results of the optical system (light-scattering photometer or absorptiometer) selected at Step S5 is reported as the final concentration. That is, the measured final concentration, together with the optical system used for measuring the concentration, is displayed on the CRT 25 and printed through the printer 22. Further, it is stored in the FD 23 and the memory 11.

Here, when $Conc._I$ and $Conc._A$ do not fall within the allowable ranges of both the optical systems (the light-scattering photometer and the absorptiometer), the sensitivity computation section 18d supplies a signal indicating the abnormality to the CRT 25 (concentration display section) and displays alarm showing the abnormality.

(5) Interference Substance Check

There is a method of checking from a data difference between the light-scattering photometer and the absorptiometer.

That is, the computation of the reported value of a concentration is decided with either the light-scattering photometer or the absorptiometer by a concentration computation logic to compare sensitivities and select a photometer as described already. When concentration dissociates between the light-scattering photometer and the absorptiometer however, there is a possibility of causing abnormality with either of the photometers. When data dissociate, alarm is generated with the CRT 25 and the like. In the judgment of data dissociation, concentration percentage or concentration difference can be selected and it is set by concentration ranges (low, middle, and high concentrations).

Whether or not dissociation occurs is judged by using the following expression (9) in the case of the percentage judgment and by using the following expression (10) in the case of the concentration judgment.

[Num-9]

$$(\text{Concentration by light-scattering photometer/concentration by absorptiometer}) \times 100\% \quad \text{Expression (9)}$$

[Num-10]

$$\text{Concentration judgment:} |\text{concentration by light-scattering photometer} - \text{concentration by absorptiometer}| \quad \text{Expression (10)}$$

In this way, in Example 1 according to the present invention, the configuration is devised so as to: be provided with a light-scattering photometer and an absorptiometer; with regard to each of the analysis items, measure it simultaneously with the two photometers of the light-scattering photometer and the absorptiometer; set an allowable range to a calibration curve; and use the concentration of the photometer having the smaller difference between the maximum concentration and the minimum concentration in the allowable range.

As a result, it is possible to: compute the concentration of an identical reaction solution by the analysis methods of an absorptiometric method and a light-scattering photometric method having different measurement principles; and measure a reagent of latex nephelometry at a higher sensitivity. Further, it is possible to provide a highly-reliable measurement result to a clinical side.

That is, it is possible to: decide an optimum photometer in accordance with a concentration range from two photometers of a light-scattering photometer and an absorptiometer; and materialize an automatic analysis apparatus and a sample measuring method, which can improve detection sensitivity.

Example 2

Example 2 according to the present invention is explained hereunder.

Although a concentration judgment flow to select a photometer by comparing sensitivity is explained in Example 1 according to the present invention, Example 2 is the example of: carrying out the operations of Steps S1, S2, S3, S8, and S9 shown in FIG. 8; and selecting a photometer from a concentration range table.

The other configurations are the same between Example 1 and Example 2 and hence detailed explanations are omitted.

In FIG. 8, a sample is measured at Steps S1, S2, and S3 and an interim concentration is computed from absorbance data by using a calibration parameter at Step S8. Then the computed concentration region is classified into three regions of low, middle, and high and a concentration range table is developed.

Successively, at Step S9, with regard to a low concentration, a middle concentration, and a high concentration, which combination of a concentration and a photometer used for measuring the concentration is selected is decided from the developed concentration range table. A concentration by scattering is selected in the low concentration region and either of a concentration by scattering or a concentration by absorbance may be selected in the middle concentration region. Further, a concentration by absorbance is selected in the high concentration region.

In Example 2 according to the present invention too, it is possible to: decide an optimum photometer in accordance with a concentration range from two photometers of a light-scattering photometer and an absorptiometer; and materialize an automatic analysis apparatus and a sample measuring method, which can improve detection sensitivity.

Here, the above examples are based on the case of using two photometers of a light-scattering photometer and an absorptiometer but the present invention is applicable also to the case of using plural photometers of other different types.

DESCRIPTION OF REFERENCE NUMERALS

1 Reaction disk
2 Reaction container
3 Constant-temperature bath
4 Constant-temperature retaining device
5 Sample disk
6 Sample container
7 Movable arm
8 Pipet nozzle
9A, 9B Reagent cool box
10A, 10B Reagent bottle
11 Memory
12A, 12B Pipet nozzle for reagent
13A, 13B Reagent dispensing mechanism
14A, 14B Light source
15A Light-scattering photometer
15B Absorptiometer
16 A/D converter
17 Reaction container cleaning mechanism
18 Computer (controller)
19 Interface
20 Sample dispensing control section
21 Reagent dispensing control section
22 Printer
23 External output medium
24 Keyboard
25 CRT display
26A, 26B Reagent disk
34A, 34B Bar-code reader

The invention claimed is:

1. An automatic analysis apparatus comprising:
a sample dispensing mechanism to intake and discharge a sample of unknown concentration contained in a sample container to a reaction container;
a reagent dispensing mechanism to intake and discharge a reagent contained in a reagent container to the reaction container;
a plurality of photometers to detect light projected from a light source to the reaction container, wherein the plurality of photometers are an absorptiometer and a light-scattering photometer;
a display; and
a controller configured to:
control operations of the sample dispensing mechanism and the reagent dispensing mechanism,
measure a blank solution and a standard solution with each of the plurality of photometers, wherein the standard solution is measured a plurality of times by each of the plurality of photometers,
create a calibration curve for each of the plurality of photometers based on the blank measurement and the plurality of measurements of the standard solution,
calculate a maximum value and a minimum value of the concentration for the standard solution for each of the plurality of photometers based on the plurality of measurements,
set an allowable concentration range of the standard solution for each of the absorptiometer and the light-scattering photometer,
determine whether the calculated maximum value and the calculated minimum value of the concentration of the standard solution fall within allowable concentration ranges associated with the absorptiometer and the light-scattering photometer,
upon the determination that the calculated maximum and minimum values fall within the allowable concentration ranges:
compute a concentration width for each of the plurality of photometers, wherein the concentration width is a difference between the calculated maximum value and the calculated minimum value of the concentration of the standard solution for the respective photometer, compare the computed concentration width of the absorptiometer with the computed concentration width of the light-scattering photometer, and based on the comparison, select the photometer having a smallest computed concentration width, control the sample dispensing mechanism to discharge the sample into the reaction container, control the reagent dispensing mechanism to discharge the reagent into the reaction container, and control the selected photometer to detect light projected from the light source through the reaction container having the sample, and decide the concentration of the sample based on the detected light from the selected photometer, and display the decided concentration of the sample and the selected photometer for measuring the concentration to a user via the display.

2. The automatic analysis apparatus according to claim 1, upon the determination that at least one of the calculated maximum and minimum values does not fall within the allowable concentration ranges, the controller is configured to display an alarm as an abnormality on the display.

3. The automatic analysis apparatus according to claim 1, wherein the automatic analysis apparatus is provided with:

a memory to store the selected photometer and the concentration.

* * * * *